United States Patent [19]

Burk

[11] Patent Number: 5,206,398

[45] Date of Patent: Apr. 27, 1993

[54] CHIRAL PHOSPHOLANE TRANSITION METAL CATALYSTS

[75] Inventor: Mark J. Burk, Hockessin, Del.

[73] Assignee: E. I. Du Pont de Nemours and Company, Wilmington, Del.

[21] Appl. No.: 904,764

[22] Filed: Jun. 26, 1992

Related U.S. Application Data

[62] Division of Ser. No. 644,526, Jan. 23, 1991, abandoned, which is a division of Ser. No. 524,737, May 17, 1990, Pat. No. 5,008,457.

[51] Int. Cl.$^5$ .......................... C07F 15/00; C07F 9/28
[52] U.S. Cl. ........................................ 556/16; 556/18; 556/20; 556/136; 568/10; 568/12
[58] Field of Search ..................... 556/136, 16, 18, 20; 568/10, 12

[56] References Cited

PUBLICATIONS

Brunner et al., Journal of Organometallic Chemistry, vol. 328, pp. 71–80 (1987).
Schrock et al., Journal of American Chemical Society, vol. 93, No. 10, pp. 2397–2407 (1971).
Wilson et al., Synlett, pp. 199–200, Apr. (1990).
Masamune et al., Journal of Organic Chemistry, vol. 54, p. 1755.

Primary Examiner—José G. Dees
Assistant Examiner—Porfirio Nazario
Attorney, Agent, or Firm—Kathleen W. Geiger

[57] ABSTRACT

Chiral 2,5-disubstituted phospholanes useful as transition metal ligands in asymmetric catalysis and processes for their preparation are disclosed.

8 Claims, No Drawings

CHIRAL PHOSPHOLANE TRANSITION METAL CATALYSTS

This is a division of application Ser. No. 07/644,526 filed Jan. 23, 1991, now abandoned and entitled Chiral Phospholane Transition Metal Catalysts which in turn is a divisional of application Ser. No. 07/524,737 filed May 17, 1990, now U.S. Pat. No. 5,008,457 entitled Chiral Phospholane Transition Metal Catalysts.

FIELD OF THE INVENTION

The invention relates to novel chiral 2,5-disubstituted phospholanes and a method for their preparation. The compounds, when complexed with transition metals, are efficient catalyst precursors for the enantioselective hydrogenation of unsaturated substrates.

BACKGROUND OF THE INVENTION

The development of novel catalytic systems exhibiting unique reactivity and high enantioselectivity requires the synthesis of chiral ligands for transition metals. Generally, some of the most successful chiral ligands have been chelating phosphines possessing a $C_2$ symmetry axis. The synthesis of these phosphines in optically pure form often involves tedious synthetic routes that are limited to only one antipode or require a resolution step.

One synthetic route is through a diol intermediate. S. Masamune et al., Journal of Organic Chemistry, Vol. 54, p. 1755 (1989) teaches use of Baker's yeast for the reduction of 2,5-hexanedione to the corresponding (S,S)-diol, followed by reaction with methanesulfonyl chloride and ring closure with benzylamine to form the optically pure (2R,5R)-2,5-dimethylpyrrolidine. Wilson et al., Synlett, pp. 199-200, April, 1990 disclose similar use of a diol intermediate formed via a Baker's yeast reduction of a diketone in the preparation of a 2,5-dimethylphospholane (Compound 10). The phospholane is prepared by reacting the diol with methanesulfonyl chloride followed by phenylphosphine in the presence of potassium hydroxide. However, enzymatic reductions generally provide only one enantiomer of the desired product, and can have limitations such as high substrate specificity, low product yields, or involved isolation procedures.

In addition, many of the chiral phosphines known in the art have at least two aryl substituents on the phosphorus, rendering that center relatively electron poor. The mechanism of asymmetric induction using these phosphines has been linked to the proper conformational relationship between the phenyl groups on the phosphorus centers.

More recently, chiral phosphines having relatively electron-rich phosphorus centers have been reported. Brunner et al., Journal of Organometallic Chemistry, Vol. 328, PP. 71-80 (1987) teach 3,4-disubstituted phospholanes derived from tartaric acid having chloro, methoxy, or dimethylamino substituents. These were complexed with manganese and rhodium and used as catalysts in the hydrogenation of alpha-N-acetamidocinnamic acid. Relatively low optical yields of (S)-N-acetylphenylalanine of from 6.6% enantiomeric excess to 16.8% enantiomeric excess were obtained.

A need exists for transition metal complexes providing high levels of stereochemical control and asymmetric induction in stoichiometric and catalytic transformations. A need also exists for efficient synthetic routes for the preparation of chiral ligands having a high degree of enantiomeric purity for transition metal catalysts.

It is therefore an object of the present invention to provide novel phospholane compounds as chiral ligands for transition metals.

It is a further object of the present invention to provide transition metal catalysts which provide high levels of stereochemical control of reactions.

It is a further object of the present invention to provide transition metal catalysts which result in high levels of asymmetric induction in hydrogenation reactions.

It is a further object of the present invention to provide efficient synthetic routes for the preparation of these phospholane compounds.

SUMMARY OF THE INVENTION

The present invention comprises phospholane compounds represented by the following formula I

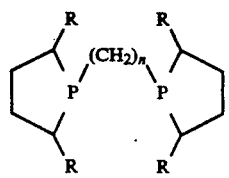

wherein:

R is a lower alkyl, trifluoromethyl, phenyl, substituted phenyl, aralkyl, or ring substituted aralkyl; and n is an integer from 1 to 12.

The present invention further comprises transition metal complexes of compounds of formula I.

A second aspect of the present invention further comprises phospholane compounds represented by the following formula II

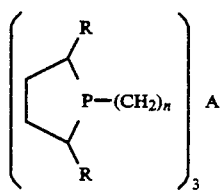

wherein R and n are as defined above for formula I, and A is $CCH_3$, CH, N or P.

The present invention further comprises transition metal complexes of compounds of formula II.

A third aspect of the present invention comprises phospholane compounds represented by the following formula III

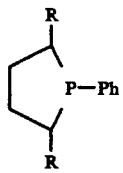

wherein:

R is an alkyl group of two to six carbon atoms, trifluoromethyl, phenyl, substituted phenyl, aralkyl, or ring substituted aralkyl.

A fourth aspect of the present invention comprises a process for the preparation of compounds of formula I as described above wherein a phenyl substituted phospholane of formula III is reacted with lithium and either 1) a dihalo compound of formula X-(CH$_2$)$_n$-X wherein X is halogen, and n is an integer from 1 to 12, or 2) a compound of formula R$^1$O(CH$_2$)$_n$OR$^1$ wherein n is an integer from 1 to 12, and R$^1$O or OR$^1$ is methanesulfonate, trifluoromethanesulfonate or p-toluenesulfonate.

A fifth aspect of the present invention comprises a process for the preparation of compounds of formula II wherein a compound of formula III as defined above is reacted with lithium and a trihalo compound of formula A[(CH$_2$)$_n$X]$_3$ wherein X is halogen, n is defined as above, and A is CCH$_3$, CH, N or P.

DETAILED DESCRIPTION OF THE INVENTION

The present invention provides chiral phospholane substituted alkanes useful as ligands for transition metals in asymmetric catalysis. The peralkylated nature of these compounds renders the phosphorus center electron rich. Transition metal complexes containing these ligands demonstrate a high level of enantioselective control and asymmetric induction in the catalyzed hydrogenation of unsaturated substrates. It has been found that the close proximity of the chirality to the metal center of the complex results in an increase of the asymmetric induction achieved.

This invention also provides an efficient stereospecific process for the preparation of the chiral phospholanes. The availability of optically active 1,4-diols with a high degree of enantiomeric purity permits preparation of optically active phospholane compounds with a high degree of enantiomeric purity.

The present invention comprises novel phospholane substituted alkane compounds of formulae I and II

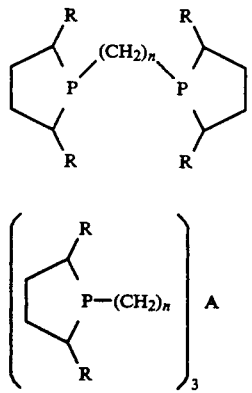

wherein for each of formula I and II:

R is a lower alkyl, trifluoromethyl, phenyl, substituted phenyl, aralkyl, or ring-substituted aralkyl; and n is an integer from 1 to 12; and for formula II, A is CCH$_3$, CH, N or P.

The present invention further comprises transition metal complexes of these compounds.

Preferred are compounds of formulae I and II wherein R is a lower alkyl of C$_1$ to C$_6$ alkyl and n is 1 to 3. Most preferred are those compounds of formula I and II wherein R is methyl and n is 1 to 3.

Examples of such compounds include, but are not limited to, 1,2-bis[(2R,5R)-2,5-dimethylphospholano]-ethane; 1,3-bis[(2R,5R)-2,5-dimethylphospholano]-propane; tris[((2S,5S)-2,5-dimethylphospholano)methyl]-methane; tris[2-([2R,5R]-2,5-dimethylphospholano)-ethyl]amine; or 1,1,1-tris[2-([2R,5R]-2,5-dimethylphospholano)ethyl]ethane.

The above phospholane compounds of formulae I and II can be complexed with any of the transition metals of Groups 3 through 12 of the periodic table, plus the lanthanides and actinides. Due to the electron-rich nature of the phospholane compounds they generally coordinate best with the transition metals of Groups 4 through 10. Such complexes are formed by methods known in the art. Preferred transition metal complexes of the present invention are those comprising the above described preferred compounds complexed with rhodium.

The phospholane compounds of formulae I and II of the present invention are useful as transition metal ligands in asymmetric catalysis. The use of these ligands in transition metal catalysts results in a high level of enantioselective and stereochemical control in the catalyzed hydrogenation of unsaturated substrates.

By a high level of enantioselectivity is meant a hydrogenation that yields a product of greater than or equal to about 80%, preferably, greater than or equal to about 90% enantiomeric excess (abbreviated ee).

Enantiomeric excess is defined as the ratio (%R−%S)(%R+%S), where %R is the percentage of R enantiomer and %S is the percentage of S enantiomer in a sample of optically active compound.

For the purpose of this application, by a "compound with a high degree of enantiomeric purity", or a "compound of high enantiomeric purity" is meant a compound that exhibits optical activity to the extent of greater than or equal to about 90%, preferably, greater than or equal to about 95% enantiomeric excess (abbreviated ee).

A further aspect of the present invention comprises the phospholane compounds of formula III

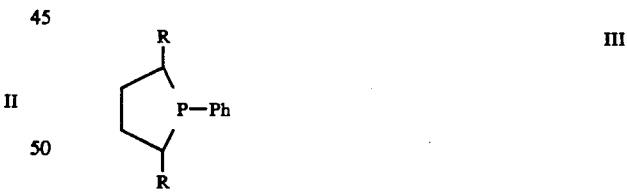

wherein R is an alkyl group having 2 to 6 carbon atoms, trifluoromethyl, phenyl, substituted phenyl, aralkyl, or ring substituted aralkyl.

Preferred compounds of formula III are those wherein R is an alkyl group of 2 to 6 carbon atoms.

The phospholane compounds of formula II of the present invention are useful as intermediates in the preparation of the compounds of formulae I and II.

Another aspect of the present invention comprises processes for the preparation of compounds of formulae I, II and III. The phospholane compounds are prepared by processes of the present invention which provide high yields and high substrate stereo-selectivity. The processes are summarized in reaction Scheme I hereinafter.

SCHEME I

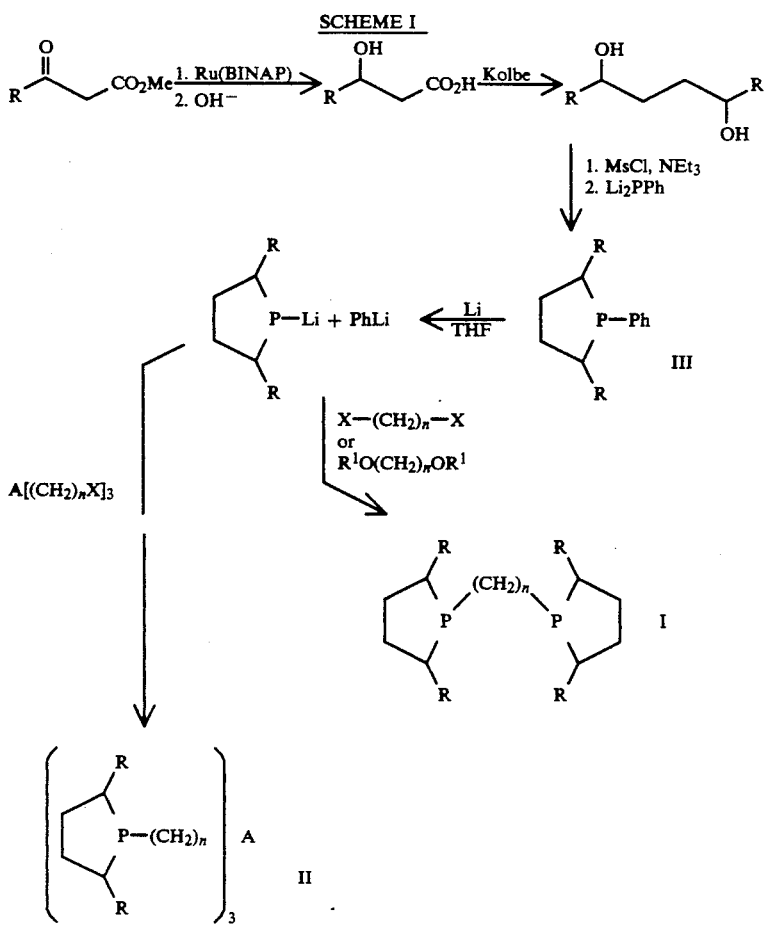

The first step introduces the desired chirality and utilizes a Ru(BINAP) [Ru-(R)-(+) or (S)-(−)-2,2′-bis(-diphenylphosphino)-1,1′-binaphthyl] catalyst as taught in Noyori et al., J. Amer. Chem. Soc., Vol. 110, p. 629 (1988), which is herein incorporated by reference, for the asymmetric reduction of a β-keto ester to the corresponding β-hydroxy ester. Hydrolysis with a strong base such as KOH provides the free carboxylic acid, which is then subjected to electrochemical Kolbe-coupling to afford a chiral diol. In the Kolbe-coupling reaction a β-hydroxy carboxylic acid of formula $R^1R^2C(OH)CH_2COOH$, wherein $R^1$ and $R^2$ are each independently hydrogen, lower alkyl, phenyl, substituted phenyl, aralkyl or ring-substituted aralkyl, or $R^1$ and $R^2$ are joined together to form a 4-, 5- or 6-membered ring, is dissolved or suspended in a lower alcohol solvent, together with a catalytic amount of a corresponding alkali metal alkoxide. Electrical current is then passed through the solution or suspenions and the chiral diol product isolated by methods known in the art. The chiral diol is reacted with an alkylsulfonyl chloride, preferably methanesulfonyl chloride, in the presence of a tertiary amine such as triethylamine to form the bis(alkylsulfonate) derivative of the diol. Dilithium phenylphosphide is then added to obtain the chiral 2,5-disubstituted-1-phenylphospholane of formula III.

The preparation of phospholane compounds of formulae I and II using the compounds of formula III requires two additional steps. Treatment of a phenylphospholane of formula III with lithium with a clean metallic surface results in selective cleavage of the phenyl group and yields a mixture of 2,5-disubstituted lithium phosphide and phenyllithium. This reaction is conducted in tetrahydrofuran or an equivalent solvent. It is conducted at a temperature range of from about 0° C. to about 40° C., preferably from about 20° C. to about 25° C. This reaction is conducted in the absence of oxygen and water under an inert atmosphere at a pressure of about 1 atm. Preferably the inert atmosphere is argon. Agitation is required since it is a heterogenous reaction with lithium metal. The overall reaction time can range from about 5 to about 30 hours, and typically is from about 10 to about 20 hours.

The resulting mixture is then reacted directly with a compound of formula $R^1O(CH_2)_nOR^1$ wherein $OR^1$ or $R^1O$ is methanesulfonate, trifluoromethanesulfonate, or p-toluenesulfonate, or with a dihalo alkane of formula $X-(CH_2)_n-X$ wherein X is halogen, preferably chloro or bromo, to obtain the desired chiral chelating bis(phospholanes) of formula I. Reacting the mixture with a compound of formula $A[(CH_2)_nX]_3$ wherein X is halogen, preferably chloro or bromo; A is $CCH_3$, CH, N or P; and n is 1 to 12; yields the desired tris(phospholanes) of formula II. These reactions are conducted at a temperature range of from about −78° C. to about 40° C., preferably at from about 0° C. to about 25° C., in tetrahydrofuran solvent. An inert atmosphere is employed, preferably argon or nitrogen at about 1 atm. pressure. The reaction mixture is agitated. The overall reaction time for these reactons is from about 0.5 to about 2 hours, typically from about 0.5 to about 1 hour. The desired product is isolated using methods well known in the art such as distillation, crystallization, evaporation of solvent, filtration, chromatography and the like.

The following examples illustrate the present invention but are not intended to limit it in any manner.

GENERAL PROCEDURES

All reactions and manipulations were performed in a nitrogen-filled Vacuum Atmospheres Dri-Lab glovebox or using standard Schlenk (inert atmosphere) techniques. Benzene, toluene, diethyl ether ($Et_2O$), tetrahydrofuran (THF), glyme, hexane, and pentane were distilled from sodium benzo-phenone ketyl under nitrogen. Acetonitrile ($CH_3CN$) and methylene chloride ($CH_2Cl_2$) were distilled from $CaH_2$. Methanol (MeOH) was distilled from $Mg(OMe)_2$.

Melting points were determined using a Mel-Temp apparatus in capillaries sealed under nitrogen and were uncorrected. HPLC analyses were performed using a Hewlett Packard Model HP 1090 LC interfaced to a HP 9000 Series 300 computer workstation. Optical Rotations were obtained using a Perkin Elmer Model Polarimeter. NMR spectra were obtained on Nicolet NT-360 wide-bore (360 MHz $^1H$, 145 MHz $^{31}P$), Nicolet NMC-300 wide-bore (300 MHz $^1H$, 120.5 MHz $^{31}P$, 75.5 Mz $^{13}C$) and Nicolet QM-300 narrow-bore (300 MHz $^1H$) spectrometers. $^{13}C$ and $^{31}P$ NMR chemical shifts were positive downfield (and negative upfield) from external $Me_4Si$ and 85% $H_3PO_4$, respectively. IR spectra were recorded on a Nicolet 5DXB FT-IR spectrometer. Elemental analyses were performed by Oneida Research Services, Inc., Whitesboro, N.Y., or Schwarzkopf Microanalytical Laboratory, Inc., Woodside, N.Y.

The precursor chiral $\beta$-hydroxy esters used in the following examples of diol synthesis were prepared as described by Noyori et al., J. Amer. Chem. Soc., 109, 5856 (1987) which is herein incorporated by reference. The asymmetric reduction of $\beta$-keto esters to the $\beta$-hydroxy esters was conducted using a ruthenium catalyst bearing the chiral phosphine ligand BINAP, (R)-(+) or (S)-(−)-2,2'-bis(diphenylphosphine)-1,1'-binaphthyl, (both enantiomers commercially available from Strem Chemicals, 7 Mulliken Way, Dexter Industrial Park, P.O. Box 108, Newburyport, Mass. 01950).

EXAMPLE 1 a) Preparation of chiral $\beta$-hydroxy acids. A mixture of methyl (3R)-3-hydroxypentanoate (290 g, 2.2 mol) in water (200 mL) and ethanol (200 mL) was cooled to 0° C. To this cold solution was added a solution of KOH (185 g, 3.3 mol) in water (1 L). The reaction was then allowed to stir at 25° C. for 48 h. The resulting solution was concentrated to ca. 500 mL and acidified (conc. HCl) until pH=1 was reached. The precipitated salts were filtered and the filtrate subjected to continuous liquid/liquid extraction with diethyl ether (1 L) for 24 h. The diethyl ether was removed on a rotovap to afford the product $\beta$-hydroxy acid as a colorless oil (250 g, 97%). The crude product was sufficiently pure to use in the next step (Kolbe-coupling).

b) Preparation of (2R,5R)-2,5-hexanediol. A 100 mL reaction vessel was charged with (3R)-3-hydroxybutyric acid (1.0 g, 9.6 mmol), methanol (30 mL) and sodium methoxide (1.0 mL of a 0.5 N solution in methanol, 0.05 mmol), and then was cooled to 0° C. Using a Pt foil anode (5 $cm^2$), a Pt screen cathode (5 $cm^2$), and a 50 V/40 amp power supply, a constant current (current density 0.25 A/$cm^2$) was applied until 1388 coulombs (1.5 F/mol) were passed. The reaction and gas evolution ($H_2$ and $CO_2$) proceeded normally until ca. 1.0 F/mol current were passed, after which the resistance was observed to increase. The colorless solution was concentrated on a rotovap. Chromatography on $SiO_2$ (70% ethyl acetate/ hexane) afforded the product as a colorless crystalline solid (0.36 g, 64%). mp 53°–54° C.; $[\alpha]^{25}D = -37.6°$ (c 1, $CHCl_3$); $^1H$ NMR $CD_2Cl_2$) $\delta$1.15 (d, $J_{HH}$=6.2 Hz, 6H $CH_3$), 1.50 (m, 4H, $CH_2$), 2.95 (br, 2H, OH), 3.75 (m, 2H, CH); $^{13}C$ NMR ($CD_2Cl_2$) $\delta$ 23.6, 35.9, 68.1.

c) Preparation of (2R,5R)-2,5-hexanediol bis(methanesulfonate). To a solution of (2R,5R)-2,5-hexanediol (8.9 g, 0.075 mol) in $CH_2Cl_2$ (200 mL) was added triethylamine (26.2 mL, 0.188 mol). The solution was cooled to 0° C., and methanesulfonyl chloride (12.82 mL, 0.166 mol) in $CH_2Cl_2$ (30 mL) was added dropwise over 30 min. Upon complete addition, the mixture containing precipitated salts was allowed to stir at 0° C. for 30 min, and then at 25° C. for 30 min. The mixture was then poured into 1N HCl (250 mL) at 0° C. After shaking, the layers were separated and the aqueous layer was extracted with $CH_2Cl_2$ (2×50 mL). The combined organic layers were washed successively with 1N HCl (50 mL), saturated $NaHCO_3$, and brine. After drying ($MgSO_4$), the solution was concentrated on a rotovap to a pale yellow oil (18.2 g, 88%). The crude product thus obtained was sufficiently pure to be used in further reactions. $^1H$ NMR ($CDCl_3$) $\delta$ 1.41 (d, $J_{HH}$=6.3 Hz, 6H $CH_3$), 1.78 (m, 4H, $CH_2$), 3.0 (s, 6H, $CH_3$), 4.85 (m, 2H, CH).

d) Preparation of (2R,5R)-2,5-dimethyl-1-phenylphospholane. To a slurry of $Li_2PPh$-THF (20.3 g, 0.105 mol) in THF (300 mL) at −78° C. was added dropwise a solution of (2S,5S)-2,5-hexanediol bis(methanesulfonate) (26.0 g, 0.095 mol) in THF (50 mL). Upon complete addition, the orange mixture was allowed to stir at −78° C. for 1 h. The reaction was then slowly warmed to 25° C. and stirring was continued for 16 h. The resulting pale yellow mixture was filtered through a coarse frit, and concentrated to a semi-solid. Extraction with pentane (100 mL) and filtration, followed by concentration in vacuo yields a pale yellow oil. Distillation afforded the product as a colorless oil (13.9 g, 76%): bp 61°–64° C. (0.2 torr); $[\alpha]^{25}D = -49.0\pm2°$ (c 1, hexane); $^1H$ NMR ($C_6D_6$) $\delta$0.70 (dd, $J_{HH}$=7.2 Hz, $J_{PH}$=10.6 Hz, 3H, $CH_3$), 1.1–1.3 (m, 2H, $CH_2$), 1.20 (dd, $J_{HH}$=7.2 Hz, $J_{PH}$=18.8 Hz, 3H, $CH_3$), 1.65 (m, 1H, CH), 2.0 (m, 2H, $CH_2$), 2.45 (m, 1H, CH); $^{31}p$ NMR ($C_6D_6$) $\delta$ 10.0; $^{13}C$ NMR ($C_6D_6$) $\delta$15.43 ($CH_3$), 21.23 (d, $J_{PC}$=34.2 Hz, $CH_3$), 32.25 (d, $J_{PC}$=10.0 Hz, CH), 35.62 (d, $J_{PC}$=13.1 Hz, CH), 37.17 ($CH_2$), 37.24 (d, $J_{PC}$=3.6 Hz, $CH_2$), 128.11, 128 30, 134.51 (d, $J_{PC}$=19.0 Hz, ortho), 137.67 (d, $J_{PC}$=28.1 Hz, ipso Ph); HRMS (EI, direct insert): m/z 192.1068 (M+, exact mass calcd for $C_{12}H_{17}P$: 192.1068), 177.0839 (M-$CH_3$), 150.0559 (M-$C_3H_6$), 135.0367 (M-$C_4H_9$), 108.0127 ($C_6H_5P$ fragment).

e) (2S,5S)-2,5-dimethyl-1-phenylphospholane $[\alpha]^{25}D = +51.6 \pm2°$ (c 1, hexane). Other spectroscopic properties were identical to Example 1 d).

f) Preparation of 1,2-Bis((2R,5R)-2,5-dimethylphospholane)ethane. To phospholane of Example 1 d) (6.0 g, 0.031 mol) in THF (200 mL) at 25° C. under Ar was added clean Li ribbon (0.54 g, 0.078 mol), and the reaction was allowed to stir for 10 h. To the resulting brown/green mixture was added dropwise a solution of ethylene glycol di-p-tosylate (6.90 g, 0.018 mol) in THF (100 mL). After stirring for 1 h, the mixture was filtered (coarse frit) and MeOH (2 mL) was added to the filtrate which turned pale yellow. The reaction was allowed to stir for 30 min and then filtered. The filtrate was concentrated to dryness in vacuo, and the resulting solids were extracted with pentane (200 mL) and filtered. The pentane filtrate was concentrated to a yellow oil which was distilled to afford the product as a colorless oil (2.10 g, 52%): bp 64°-67° C. (0.06 torr); $[\alpha]^{25}D = +222\pm6°$ (c 1, hexane); 1H NMR ($C_6D_6$) $\delta0.98$ (dd, $J_{HH}=7.2$ Hz, $J_{PH}=9.1$ Hz, 3H, $CH_3$), 1.0–1.35 (m, 5H, $CH_2$), 1.22 (dd, $J_{HH}=7.2$ Hz, $J_{PH}=17.3$Hz, 3H, $CH_3$), 1.55 (m, 2H, CH, $CH_2$), 1.70 (m, 5H, CH, $CH_2$), 1.90 (m, 4H, CH, $CH_2$); 31P NMR ($C_6D_6$) $\delta3.2$; 13C NMR ($C_6D_6$) $\delta14.6$ ($CH_3$), 20.71 (d, $J_{PC}=6.0$ Hz, $CH_3$), 21.48 (dd, $J_{PC}=15.5$ Hz, bridge $CH_2$), 34.44 (dd, $J_{PC}=5.8$, 5.9 Hz, ring CH), 37.02 (ring $CH_2$), 37.42 (ring $CH_2$), 38.32 (dd, $J_{PC}=5.5$ Hz, ring CH); HRMS (EI, direct insert): m/z 258.1670 (M+, exact mass Calcd for $C_{14}H_{28}P_2$: 258.1667), 230.1344 (M-$C_2H_4$), 175.0785 (M-$C_6H_{11}$), 144.1072 (M-$C_6H_{11}P$), 116.0748 (M-$C_8H_{15}P$). g) Optical Purity of Phosphines. The phosphines of Example 1 d), e) and f) were ascertained to be optically pure (within the limits of detection) by reacting each with (R)-[dimethyl-(α-methylbenzyl)-aminato-C,N]palladium (II) chloride dimer and monitoring the 31P NMR spectrum. Comparisons were made with the spectrum of the opposite phosphine enantiomer.

EXAMPLE 2

Preparation of 1,3-Bis((2R,5R)-2,5-dimethylphospholano)propane. To phospholane of Example 1 d) (6.0 g, 0.031 mol) in THF (200 mL) at 25° C. under Ar was added clean Li ribbon (0.54 g, 0.078 mol), and the reaction was allowed to stir for 10 h. To the resulting brown/green mixture was added dropwise a solution of 1,3-dichloropropane (2.11 g, 0.018 mol) in THF (25 mL). The reaction decolorized towards the end of the addition, and after stirring for 30 min, MeOH (2 mL) was added. This mixture was allowed to stir 10 min, then was filtered, and the filtrate concentrated in vacuo. The resulting oil was extracted with pentane (125 mL), filtered, and the pentane layer was concentrated to a yellow oil. Distillation afforded the product as a colorless oil (3.2 g, 75%): bp 98°-101° C. (0.08 torr); $[\alpha]^{25}D = +-279 \pm6$ (c 1, hexane); 1H NMR ($C_6D_6$) $\delta1.0$ (dd, $J_{HH}=7.1$ Hz, $J_{PH}=9.6$ Hz, 3H, $CH_3$), 1.05 (m, 2H, $CH_2$), 1.20 (dd, $J_{HH}=7.1$ Hz, $J_{PH}=17.5$ Hz,3H, $CH_3$), 1.20 (m, 2H, $CH_2$), 1.40 (m, 2H, $CH_2$), 1.55 (m, 4H, $CH_2$), 1.70 (m, 4H, CH, $CH_2$), 1.90 (m, 4H, CH, $CH_2$); 31P NMR ($C_6D_6$) $\delta-2.85$; 13C NMR ($C_6D_6$) $\delta14.6$ ($CH_3$), 21.45 (d, $J_{PC}=30.8$ Hz, $CH_3$), 24.34 (t, $J_{PC}=18.9$ Hz, bridge central $CH_2$), 25.70 (dd, $J_{PC}=11.3$, 22.3 Hz, bridge $CH_2$), 34.05 (d, $J_{PC}=12.1$ Hz, ring CH), 37.10 (d, $J_{PC}=3.6$ Hz, ring $CH_2$), 37.51 (ring $CH_2$), 38.30 (d, $J_{PC}=11.5$ Hz, ring CH); HRMS (EI, direct insert): m/z 272.1816 (M+exact mass calcd for $C_{15}H_{30}P_2$: 272.1823), 229.1283 (M-$C_3H_7$), 188.0831 (M-$C_6H_{12}$), 157.1139 (M-$C_6H_{12}P$), 130.0900 (M-$C_8H_{15}P$), 116.0742 ($C_6H_{13}P$ fragment).

Optical Purity. The phosphine of Example 2 was ascertained to be optically pure (within the limits of detection) by reacting it with (R)-[dimethyl-(α-methylbenzyl)-aminato-C,N]palladium (II) chloride dimer and monitoring the 31P NMR spectrum. Comparisons were made with the spectrum of the opposite phosphine enantiomer.

EXAMPLE 3 a) Rhodium complex [(COD)Rh(1,3-bis((2R,5R)-2,5-dimethylphospholano)propane)]+$PF_6^-$. To a mixture of [(COD)RhCl]$_2$ (0.44 g, 0.89 mmol, COD=1,5-cyclooctadiene) and Na$PF_6$ (0.40 g, 2.4 mmol) in THF (20 mL) at 25° C. was added dropwise a solution of 1,3-bis((2R, 5R)-2,5-dimethylphospholano)propane (0.50 g, 1.8 mmol) in THF (5 mL). The solution turned orange from yellow upon the phosphine addition. The reaction was allowed to stir for 30 min, and then was concentrated to a volume of ca. 5 mL. The slow addition of $Et_2O$ (30 mL) to the solution produced an orange precipitate which was filtered, washed with $Et_2O$, and briefly dried. The solids were dissolved in $CH_2Cl_2$ (5 mL), filtered, and $Et_2O$ (30 mL) was added slowly to the orange filtrate to provide the product as an orange microcrystalline solid (0.86 g, 75%); 1H NMR ($CD_2Cl_2$) $\delta1.15$ (dd, $J_{HH}=6.9$ Hz, $J_{PH}=14.8$ Hz, 6H, $CH_3$), 1.50(dd, $J_{HH}=7.2$ Hz, $J_{PH}=18.7$ Hz, 6H, $CH_3$), 1.3–1.6 (m, 6H, $CH_2$), 1.80 (m, 2H, CH, $CH_2$), 2.10 (m, 4H, CH, $CH_2$), 2.20–2.60 (m, 12H, $CH_2$, CH), 4.80 (m (br), 2H, COD-CH), 5.15 (m (br), 2H, COD-CH); 31 P NMR ($CD_2Cl_2$) $\delta27.7$ (d, $J_{RhP}=139.6$ Hz), −145 (sept., $PF_6$); Anal. Calcd for $C_{23}H_{42}F_6P_3Rh$: C, 43.96; H, 6.74. Found: C, 44.19; H, 6.43.

b) Rhodium complex [(COD)Rh((2R,5R)-2,5-dimethyl-1-phenylphospholane)$_2$]+$SbF_6^-$. This complex was prepared in a manner analogous to that of Example 3 a). 1H NMR ($CD_2Cl_2$) $\delta0.70$ (dd $J_{HH}=6.9$ Hz $J_{PH}=13.8$ Hz, 6H $CH_3$), 1.00 (m, 2H, $CH_2$), 1.40 (m, 2H, $CH_2$), 1.62 (dd, $J_{HH}=7.2$ Hz, $J_{PH}=18.6$ Hz, 6H, $CH_3$), 1.90 (m, 2H, $CH_2$, CH), 2.20 (m, 6H, $CH_2$, CH), 2.40 (M, 8H, COD-$CH_2$), 4.90 (br, 2H, COD-CH), 5.34 (br, 2H, COD-CH), 7.0 (m, 4H, Ph), 7.30 (m, 4H, Ph), 7.40 (m, 2H, Ph); 31 P NMR ($CD_2Cl_2$) $\delta43.8$ (d, $J_{RhP}=143.4$ Hz). Anal. calcd. for $C_{32}H_{46}P_2F_6SbRh$: C, 46.23; H, 5.58; P, 7.45. Found: C, 46.26; H. 5.47; P, 7.43.

X-ray Crystallographic Analysis. Crystal data for $C_{32}H_{46}F_6P_2RhSb$: monoclinic, P21 (No. 4), a=12.18-4(a) Åb=12.734(2) Å, c=10.771(1) Å. $\beta=96.83(1)°$, T=−100° C., V=1659.3 Å$^3$, Mo Kαradiation, $\mu_{calcd}=14.58$ cm$^{-1}$, $d_{calcd}=1.664$ gcm$^{-3}$, Z=2, FW=831.33.

Suitable Crystals of the rhodium complex were obtained by slow vapor diffusion of $Et_2O$ into a $CH_2Cl_2$ solution at 25° C. An orange needle of dimensions 0.16×0.32×0.38 mm was mounted in a nitrogen-filled thin-walled glass capillary, and data was collected on a Syntex R3 diffractometer at −100° C. The unit cell dimensions were determined by least squares refinement of 49 reflections. The crystal stability was monitored throughout the data collection by measuring the intensity of three standard reflections every 180 data points. The data were adjusted for a 2% decrease in intensity over the course of data acquisition. Lorentzian, polarization and absorption (azimuthal) corrections were applied, due to the relatively large absorption coefficient $\mu$(Mo)−14.58 cm$^{-1}$.

The structure was solved using direct methods (SHELXS). All hydrogen atoms were determined from difference Fourier maps and idealized (C-H=0.95 Å). Anisotropic refinement was carried out by full-matrix least squares on F.

Neutral atom scattering factors and anomalous scattering terms for P, Rh, and Sb were obtained from the International Tables for X-ray Crystallography, Vol. IV, herein incorporated by reference. Non-hydrogen atoms were refined anisotropically, and the hydrogens were refined isotropically for a total of 378 parameters. The refinement converged at R=0.035, $R_w$=0.041, and EOF=1.61 for 6845 unique reflections with 1 >3.0$\sigma$(1). Fractional coordinates and isotropic thermal parameters for all non-H atoms were provided in Table S-1, while anisotropic thermal parameters were given in Table S-2. A complete listing of bond lengths and angles were also supplied.

The structure consisted of discrete molecules in which the usual square planar geometry of Rh(I) was somewhat distorted. The molecule had $C_2$ symmetry, but the 1,5-cyclooctadiene ring was rotated out of the P-Rh-P plane by 17.1 degrees. This distortion was the result of interactions with the methyl groups of the phosphine ligands. The Rh-C distances also were disparate with C1 and C5 being closer than C2 and C6. The rather large thermal motion of the phenyl rings and the fluorine atoms were self-evident and limited the quality of the structure. Attempts to refine the hydrogen atoms were unsatisfactory and these atoms were idealized and fixed with isotropic thermal parameters one higher than their associated carbon atoms. A full hemisphere of data was used in the refinement of the structure; the enantiomorphic structure refined to higher values R=0.039 and $R_w$=0.048.

c) Rhodium complex [(COD)Rh-Bis((2R,5R)-2,5-dimethylphospholano)ethane]$^+$SbF$_6^-$. This complex was prepared in a manner analogous to that of Example 3 a). $^1$H NMR (CD$_2$Cl$_2$) $\delta$1.20 (dd, $J_{HH}$=6.9 Hz, $J_{PH}$=14.4 Hz, 6H, CH$_3$), 1.40 (dd, $J_{HH}$=7.1 Hz, $J_{PH}$=17.7 Hz, 6H, CH$_3$), 1.3-1.6 (m, 6H, CH$_2$), 1.95 (m, 2H, CH, CH$_2$), 2.10-2.60 (m, 10H, CH$_2$, CH), 4.95 (br, 2H, COD-CH), 5.40 br, 2H, COD-CH); $^{31}$P NMR (CD$_2$Cl$_2$) $\delta$76.7 (d, $J_{RhP}$=146.3 Hz). Calcd for C$_{22}$H$_{40}$F$_6$P$_2$SbRh C, 37.47; H, 5.72. Found: C, 37.64; H, 5.37.

X-ray Crystallographic Analysis. Suitable crystals of the rhodium complex were obtained by slow crystallization from a CH$_2$Cl$_2$/hexane (2/1) solution at 25° C. An orange needle of dimensions 0.10×0.12×0.71 mm was mounted in a nitrogen-filled thin-walled glass capillary, and data was collected on a Syntex R3 diffractometer at −100° C. The unit cell dimensions were determined by least squares refinement of 49 reflections. The crystal stability was monitored throughout the data collection by measuring the intensity of three standard reflections every 182 data points. The data were adjusted for a 4% decrease in intensity over the course of data acquisition. Lorentzian, polarization and absorption (azimuthal) corrections were applied, due to the relatively large absorption Coefficient $\mu$(Mo)=17.72 cm$^{-1}$.

The structure was solved using direct methods (SHELXS). All hydrogen atoms were determined from difference Fourier maps and idealized (C-H - 0.95 Å). Anisotropic refinement was carried out by full-matrix least squares on F. Neutral atom scattering factors and anomalous scattering terms for P, Rh, and Sb were obtained from the International Tables for X-ray Crystallography, Vol. IV, herein incorporated by reference. Non-hydrogen atoms were refined anisotropically, and the hydrogens were refined isotropically for a total of 289 parameters. The refinement converged at R=0.038, $R_w$=0.036, and EOF=1.07. Fractional coordinates and isotropic thermal parameters for all non-H atoms were provided in Table S-1, while anisotropic thermal parameters were given in Table S-2. A complete listing of bond lengths and angles were also supplied.

Like the Rh complex of Example 3 a), this structure consisted of discrete molecules in which the usual square planar geometry was distorted to an even greater extent. The complex had essentially $C_2$ symmetry with the 1,5-cyclooctadiene ligand rotated well out of the P-Rh-P plane by 24.3 degrees.

EXAMPLE 4

Hydrogenation Procedure. In a dry box, a 100 mL Fisher-Porter tube was charged with substrate (1.26 mmol), dry degassed MeOH or THF (20 mL), and the catalyst of Example 3 a), b) or c) (0.2 mol %). After two freeze-pump-thaw cycles, the tube was pressurized to an initial pressure of 10 psig with H$_2$ (Matheson, 99.998%). The reactions were allowed to stir at 25° C. for 3-12 h. Hydrogen uptake was monitored and complete reaction was indicated by GC and NMR analyses. Reactions were worked-up as previously described. Enantiomeric excesses were determined by HPLC (methyl acetamidophenylalanine, Chiralcel OB, 5% IPA/Hexane) or shift reagent (dimethyl methylsuccinate, (+)-Eu(hfc)$_3$) analyses. The resulting data is listed in Table I.

TABLE I

| Substrate | Enantiomeric Excess |
|---|---|
| Methyl acetamidocinnamate | 85% |
| Dimethyl itaconate | 91% |

EXAMPLE 5

Preparation of Tris[((2S,5S)-2,5-dimethylphospholano)methyl]methane. To (2S,5S)-2,5-dimethyl-1-phenylphospholane (6.07 g, 0.032 mol) in THF (200 mL) at 25° C. under Ar was added clean Li ribbon (0.55 g, 0.079 mmol), and the reaction was allowed to stir for 15 h. To the resulting brown-orange mixture was added dropwise a solution of 1,3-dichloro-2-(chloromethyl)-propane (1.70 g, 10.5 mmol) in THF (15 mL) at 25° C. The reaction remained brown throughout the addition, and after stirring for 30 min, MeOH (3 mL) was added. The resulting colorless mixture was allowed to stir 15 min, then was filtered through a celite pad, and the filtrate concentrated in vacuo. The resulting solids were extracted with pentane (125 mL), filtered, and the pentane layer was concentrated to ca. 15 mL. Rapid filtration afforded the product as a colorless crystalline solid (1.0 g). The filtrate was then concentrated to a pale yellow solid which was dissolved in a minimum amount of Et$_2$O (3 mL). To this solution was added MeOH (15 mL) and the mixture was cooled to −20° C. for 12 h. The resulting white crystals were filtered, washed with cold MeOH and dried in vacuo (1.65 g). Combined yield 2.65 g (63%): [$\alpha$]$^{25}$D=−329±6° (c 1, hexane); $^1$H NMR (C$_6$D$_6$) $\delta$1.0-1.2 (m, 3H, CH, CH$_2$), 1.07 (dd, $J_{HH}$=7.2 Hz, $J_{PH}$=9.8 Hz, 9H, CH$_3$), 1.29 (dd, $J_{HH}$=7.0 Hz, $J_{PH}$=17.6 Hz, 9H, CH$_3$), 1.40 (m, 3H, CH, CH$_2$), 1.60 (m, 3H, CH, CH$_2$), 1.80 (m, 3H, CH, CH$_2$), 1.9-2.2 (m, 13H, CH, CH$_2$); $^{31}$P NMR (C$_6$D$_6$) $\delta$−8.0; $^{13}$C NMR (C$_6$D$_6$) $\delta$14.89 (CH$_3$), 21.51 (d, $J_{PC}$=30.7 Hz, CH$_3$), 31.85 (dt, $J_{PC}$8.3, 22.1 Hz, bridge P-CH$_2$), 32.67 (q, $J_{PC}$=14.9 Hz, bridge CH) 34 12 (d $J_{PC}$=11.6 Hz, ring CH), 37.30 (d, $J_{PC}$=3.8 Hz, ring CH$_2$), 37.47 (ring CH$_2$), 38.49 (d, $J_{PC}$=11.3 Hz, ring CH); HRMS (EI, direct insert): m/z 400 2583 (M+ exact mass calcd for C$_{22}$H$_{43}$P$_3$: 400.2578), 357.2021 (M-C$_3$H$_7$), 315.1557 (M-C$_6$H$_{13}$), 285.1896 (M-C$_6$H$_{12}$P), 273.1104 (M-C$_9$H$_{19}$), 232.0678 (M-C$_{12}$H$_{24}$), 201.0955 (M-C$_{12}$H$_{24}$P).

EXAMPLE 6

Preparation of Tris(2-((2R,5R)-2,5-dimethyl-phospholano)ethyl)amine. To (2R,5R)-2,5-dimethyl-1-phenylphospholane (3.0 g, 15.6 mmol) in THF (100 mL) at 25° C. under Ar was added clean Li ribbon (0.27 g, 39.0 mmol), and the reaction was allowed to stir for 15 h. To the resulting brown/orange mixture was added dropwise a solution of tris(2-chloroethyl)amine (1.06 g, 5.2 mmol) in THF (15 mL) at 25° C. The reaction remained brown throughout the addition, and after stirring for 30 min, MeOH (3 mL) was added. The resulting colorless mixture was allowed to stir 15 min, then was filtered through a celite pad, and the filtrate concentrated in vacuo. The resulting solids were extracted with pentane (125 mL), filtered, and the pentane layer was concentrated to ca. 15 mL. Rapid filtration afforded the product as a colorless crystalline solid (0.6 g). The filtrate was then concentrated to a pale yellow solid which was dissolved in a minimum amount of $Et_2O$ (3 mL). To this solution was added MeOH (10 mL) and the mixture was cooled to $-20°$ C. for 12 h. The resulting white crystals were filtered, washed with cold MeOH and dried in vacuo (1.13 g). Combined yield 1.73 g (75%): $[\alpha]^{25}D = +167 \pm 2$(C 1, hexane); $^1$H NMR $C_6D_6$ $\delta$1.0–1.2 (m, 3H, CH, $CH_2$), 1.11 (dd, $J_{HH}$=7.2 Hz, $J_{PH}$=9.8 Hz, 9H, $CH_3$), 1.32 (dd, $J_{HH}$=7.0 Hz, $J_{PH}$=17.7 Hz, 9H, $CH_3$), 1.30 –1.45 (m, 3H, CH, $CH_2$), 1.55 (m, 3H, $CH_2$), 1.70–2.15 (m, 15H, CH, $CH_2$), 2.80 (m, 6H, $NCH_2$); $^{31}$P NMR ($C_6D_6$) $\delta$−3.4.

EXAMPLE 7

Preparation of 1,1,1-Tris(2-((2R,5R)-2,5-dimethyl-phospholano)ethyl)ethane. To (2R,5R)-2,5-dimethyl-1-phenylphospholane (0.53 g, 2.76 mmol) in THF (10 mL) at 25° C. under Ar was added clean Li ribbon (0.048 g, 6.9 mmol), and the reaction was allowed to stir for 15 h. To the resulting brown/orange mixture was added dropwise a solution of 1,1,1-tris(2-chloroethyl)ethane (0.2 g, 0.92 mmol) in THF (5 mL) at 25° C. The reaction remained brown throughout the addition, and after stirring for 30 min, MeOH (1 mL) was added. The resulting colorless mixture was allowed to stir 15 min, then was filtered through a celite pad, and the filtrate concentrated in vacuo. The resulting solids/oil were extracted with pentane (50 mL), filtered, and the pentane layer was concentrated to yield the product as a colorless, viscous oil (0.257 g, 61%): $^1$H NMR ($C_6D_6$) $\delta$0.84 (s, 3H, $CH_3$), 1.11 (dd, $J_{HH}$=6.9 Hz, $J_{PH}$=9.8 Hz, 9H, $CH_3$), 1.20 (dd $J_{HH}$=7.2 Hz $J_{PH}$=17.6 Hz 9H $CH_3$), 1.00–1.50 (m, 18H, CH, $CH_2$), 1.80 (m, 3H, $CH_2$), 1.90–2.15 (m, 9H CH, $CH_2$); $^{31}$P NMR ($C_6D_6$) $\delta$0.3; HRMS (EI direct insert): m/z 456.3170 (M+ exact mass calcd for $C_{26}H_{51}P_3$: 456.3204), 371.2206 (M-$C_6H_{13}$), 341.2645 (M-$C_6H_{12}P$), 257.1612 (M-$C_{12}H_{24}P$).

What is claimed is:

1. A complex comprising one or more transition metals, lanthanides or actinides and one or more of the following compounds as ligands

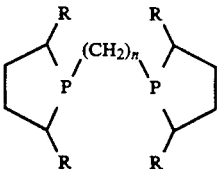

wherein:

R is a lower alkyl, trifluoromethyl, phenyl, substituted phenyl, aralkyl or ring-substituted aralkyl; and n is an integer having a value from 1 to 12.

2. The complex of claim 1 wherein the transition metal is rhodium.

3. The transition metal complex of claim 2 which is [(COD)Rh-bis[(2R,5R)-2,5-dimethylphospholano]-ethane]$^{30}$ $SbF_6^-$.

4. The transition metal complex of claim 2 which is [(COD)Rh-1,3-bis[(2R,5R)-2,5-dimethylphospholano]-propane]+$PF_6^-$.

5. A process for the preparation of a compound of formula I

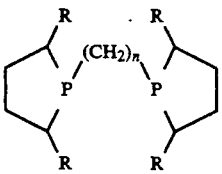

wherein:

R is a lower alkyl, trifluoromethyl, phenyl, substituted phenyl, aralkyl or ring-substituted aralkyl; and n is an integer of 1 to 12; comprising reacting a phenyl substituted phospholane of formula III

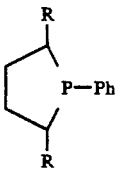

wherein R is defined as in formula I, with lithium and a dihalo compound of formula $$X-(CH_2)_n-X \text{ or } R^1O-(CH_2)_n-OR^1$$

wherein X is halogen, $OR^1$ or $R^1O$ are methanesulfonate, trifluoromethanesulfonate or p-toluenesulfonate, and n is an integer from 1 to 12 to yield the desired compound of formula I.

6. The process of claim 5 conducted in tetrahydrofuran as a solvent.

7. The process of claim 5 conducted at a temperature of from about 0° C. to about 40° C.

8. The process of claim 5 conducted in an inert atmosphere.

* * * * *